United States Patent [19]

Michel et al.

[11] Patent Number: 5,312,751
[45] Date of Patent: May 17, 1994

[54] HYBRIDOMA PRODUCING A MONOCLONAL ANTIBODY SPECIFIC FOR AN ANTIGEN OF THE STRATUM CORNEUM OF HUMAN EPIDERMIS

[75] Inventors: Serge Michel, Antibes; Jacques Bailly, Biot; Gaelle Saintigny, Nice; Uwe Reichert, Le Bar S/Loup, all of France

[73] Assignee: Centre International de Recherches Dermatologiques Galderma (Cird Galderma), Valbonne, France

[21] Appl. No.: 652,073

[22] Filed: Feb. 7, 1991

[30] Foreign Application Priority Data

Feb. 8, 1990 [FR] France .................................. 90 01462

[51] Int. Cl.$^5$ .................... C12N 5/18; C12N 15/02; C07K 15/28; C12P 21/08
[52] U.S. Cl. ........................... 435/240.27; 530/388.2; 435/70.21; 435/172.2
[58] Field of Search ................... 530/388.2, 391.1; 435/240.27, 70.21, 172.2; 424/85.8, 450, 85.91, 88

[56] References Cited

U.S. PATENT DOCUMENTS

| | | | |
|---|---|---|---|
| 4,510,244 | 4/1985 | Parks et al. | 435/172.2 |
| 4,598,051 | 7/1986 | Papahadjopoulos et al. | 436/512 |
| 4,649,115 | 3/1987 | Safai et al. | 435/240.27 |
| 4,668,638 | 5/1987 | Janoff | 436/506 |

FOREIGN PATENT DOCUMENTS 2606033 6/1988 France .
2606034 6/1988 France .

OTHER PUBLICATIONS

Wright et al. Advanced Drug Delivery Reviews 3:343-389 1989.
Waldmann, Science 252:1657-1662, 1991.
Hintner et al., J. Invest. Dermatol. 82:491-495, 1984.
Vincent et al. Clin. Exp. Immunol., 81:83-89, Jul. 1990.
Goding, "Monoclonal Antibodies", Academic Press, 1983, pp. 188-205.
Dale et al. J. Invest. Dermatol. 88:306-313, 1987.
Sevier et al. Clin. Chem. 27:1797-1806, 1981.
Rice et al. Cell 11:417-422, 1977.
Biological Abstract 87(12):126729, Tezuka et al., Arch. Dermatol. Res. 280:462-468 1989.
Chemical Abstracts vol. 111:37590d, Takahashi et al. Nippon Hifuka Gakkal Zasshi 99(2)111-16, 1989.

Primary Examiner—Paula K. Hutzell
Attorney, Agent, or Firm—Cushman, Darby & Cushman

[57] ABSTRACT

The subject invention relates to monoclonal antibodies which react with antigenic determinants which are present of the status corneum of human epidermis. Furthermore, the invention also relates to methods of using such monoclonal antibodies in immunoassays. One monoclonal antibody of the present invention which is particularly useful is BC 21.

2 Claims, No Drawings

HYBRIDOMA PRODUCING A MONOCLONAL ANTIBODY SPECIFIC FOR AN ANTIGEN OF THE STRATUM CORNEUM OF HUMAN EPIDERMIS

BACKGROUND OF THE INVENTION

1. Field of the Invention

The subject invention relates to monoclonal antibodies reactive with antigenic determinants present on the stratum corneum of human epidermis and uses thereof.

In particular, the invention relates to a monoclonal antibody, referred to as BC 21, which is useful as reagent in the treatment and diagnosis of dermatological diseases and diseases of the internal epithelia.

2. Background Information

It is known that the epidermis contains a basal membrane on which rest a layer of proliferative basal cells and layers of suprabasal cells, comprising the stratum spinosum and the stratum granulosum. These are layers of cells undergoing differentiation which become gradually keratinized and ultimately form, on the skin surface, a corneous layer (stratum corneum) composed of dead, completely keratinized cells, i.e., corneocytes. Corneocytes are formed mainly from keratin filaments which are enclosed by a very strong membrane called the corneous sheath. This corneous sheath is formed by precursor proteins linked by covalent bonds when acted upon by a specific enzyme called transglutaminase.

To study skin diseases, for example, psoriasis, acne, warts, papillomas and cancers, differentiation of the normal cells of the epidermis called keratinocytes must be better understood. As defined in the present invention, the term "normal" signifies "non-pathological." In order to undertake these studies, various markers of the terminal differentiation of the keratinocytes must be made available. A need exists in the field to identify terminal differentiation markers of the epidermis with antibodies specific for these determinants.

The present invention discloses the preparation and characterization of antibodies capable of recognizing antigenic determinants found on stratum corneum of normal human epidermis origin. Antibodies of this type are capable of reacting specifically with the stratum corneum on a non-pathological section of human epidermis. These new antibodies are potentially useful for the treatment and diagnosis of many forms of keratinization disorders such as ichthyosis, psoriasis and eczema.

SUMMARY OF THE INVENTION

It is a general object of the present invention to provide antibodies specific for antigenic determinants expressed on the stratum corneum and uses thereof.

In particular, the present invention relates to antibodies specific for the stratum corneum on a section of non-pathological human epidermis.

In another embodiment, the present invention relates to antibodies specific for the stratum corneum of human epidermis affected by keratinization disorders such as ichthyosis or photo-induced cutaneous aging, psoriasis or eczema.

In yet another embodiment, the present invention relates to antibodies characterized by their discontinuous labeling of the tritium corneum of the epidermis in the intercorneocytic space using electron microscopy detection.

In yet another embodiment, the present invention relates to antibodies specific for human keratinized epithelial tissue.

A further embodiment of the present invention relates to a hybridoma which produces a monoclonal antibody specific for an antigen that is characterized by expression on stratum corneum of normal human epidermis.

The present invention also relates to a monoclonal antibody specific for an antigen determinant having the above properties. The class of the monoclonal antibody is IgM.

The present invention also relates to a hybridoma (strain CIRD BC 21) having the accession number of 89091901 deposited on Sep. 19, 1989 at the European Collectors of Animal Cell Cultures located at the PHLS Centre for Applied Microbiology & Research—Porton Down, Salisbury, Wilts SP4 0JG, United Kingdom. The monoclonal antibody produced by accession number 89091901 is CIRD BC 21.

In another embodiment, the present invention relates to methods of preparing hybridoma cell lines that produce monoclonal antibodies specific for the stratum corneum.

A further embodiment of the present invention relates to the preparation of polyclonal antibodies characterized by their specific binding to stratum corneum.

In yet another embodiment, the present invention relates to a method of diagnosing normal or pathological differentiation of cells from the epidermis and internal epithelia in a patient comprising the steps of removing a tissue or cell sample from a patient, adding an antibody with the above identified properties to the sample and visualizing the presence or absence of the antibody in the sample.

A further embodiment of the present invention relates to a method for diagnosing keratinization disorders in a patient following the steps described above.

In another embodiment, the present invention relates to a method of treating keratinization disorders in patients by administering to the patient a conjugate comprising antibodies specifically for stratum corneum covalently linked to colloided vectors such as lyposomes or micropheres that contain a biologically active substance such as methotrexate or a diagnostic agent.

In yet another embodiment, the present invention relates to a pharmaceutical composition comprising the specific antibody covalently linked to colloidal vectors such as liposomes or microspheres in a concentration sufficient to treat a keratinization disorder.

Various other objects and advantages of the present invention will become apparent from the tables and the following description of the invention.

All publications mentioned herein are incorporated by reference.

DETAILED DESCRIPTION OF THE INVENTION

The present invention relates to antibodies, specifically monoclonal antibodies, that react with antigenic determinants present on the stratum corneum. The present invention further relates to methods utilizing the antibodies.

One embodiment of the present invention relates to antibodies, in particular, those pocessing at least one of the following properties:

they recognize the stratum corneum of the human epidermis affected by keratinization disorders such as ichthyosis or photo-induced cutaneous aging, these disorders possibly presenting, furthermore, an inflammatory component, as in the case of psoriasis or eczema;

they provide discontinuous labeling of the stratum corneum of the epidermis in the intercorneocytic space of, for example, non-pathological human epidermis in immunolabeling detection methods using electron microscopy;

they recognize human keratinized epithelial tissues;

they recognize the stratum corneum of the epidermis of at least one mammal other than man.

The present invention also relates to monoclonal antibodies which recognize a specific antigen of the stratum corneum of normal human epidermis, the antigen being that which is recognized by the BC 21 monoclonal antibody. The BC 21 nonclonal antibody which recognizes the specific antigen of the stratum corneum may be easily selected by simple routine experiments, for example, by competition tests.

The present invention also relates to antibodies that may be polyclonal, or monoclonal. These antibodies are markers of the terminal differentiation of keratinocytes.

The present invention further relates to the antibodies previously described that are modified by labeling with a tracer agent, using methods of preparation of these labeled antibodies known in the art. For example, the tracer may be a radiolabel, fluorescent label, or enzymatic tracer. Labeling with a radioactive tracer may be achieved by bonding with a radioactive isotope such as iodine or indium. Bonding antibodies with a fluorochrome (e.g., fluorescein or rhodamine isothiocyanate) or with an enzyme is also conventionally known. The enzyme may, for example, be peroxidase or an alkaline phosphatase. The enzymatic activity potentially present on the reagent after completion of the test may be determined using an appropriate substrate which may be detected by means of, for example, colorimetry, fluorescence, luminescence and potentiometric analysis.

The present invention further relates to labeled and unlabeled antibodies such as those described above, attached to a solid substrate allowing their use as immunoadsorbent agents in affinity chromatography methods or as reagents in analytical methods based on the antigen-antibody reaction (radioimmunological, immunofluorescence, and immunoenzymatic techniques).

One skilled in the art will appreciate that the solid substrate may be produced using any solid, biological, or synthetic material possessing adsorbent properties or possessing the capability of fixing a linking agent. Among the solid materials capable of bonding antibodies by adsorption are, for example, polystyrene, polypropylene and latex. The solid materials which may be used to fix the antibodies by covalence using a linking agent are made of, for example, dextran, cellulose and their amino derivatives such as diethylaminoethyl-cellulose or diethylaminoethyl-dextran. The solid substrate may exist, for example, in the form of microtitration disks, tubes, strips, balls, or plates. The linking agents utilized to fix the antibodies on the solid support by covalence are generally known in the art; they are bifunctional derivatives such as dialdehydes and quinones. One skilled in the art will also appreciate that the antibodies may be bonded in conventional ways on solid mineral substrates.

The present invention also relates to a method for preparing antibodies such as those specified above. In the preparation of both monoclonal and polyclonal antibodies having one or several of the above-mentioned properties, a vertebrate animal is immunized using purified corneous sheaths from mammal epidermis. The monoclonal or polyclonal antibodies are collected, purified and selected out using methods known in the art. The epidermis supplying the immunization agent is preferably a non-pathological, and especially a human epidermis.

Mammals whose epidermal corneous sheaths are used as immunization agents in the procedure described above can be easily determined by routine experiments by immunizing animals using purified corneous sheaths taken from a mammal, and by determining whether the antibodies thus produced contain antibodies such as those specified above. Among the mammals, exclusive of man, whose corneous epidermal sheaths can be used for immunization include, in particular, rats, rabbits and miniature pigs. The vertebrate animal immunized is of a species different from that of the mammal from which the immunization agent is taken.

The purified corneous sheaths used for immunization may be prepared from human or animal epidermis or stratum corneum. For this purpose, the sample is treated several times by successive incubations at 90° in solutions of sodium dodecyl sulfate (SDS) containing beta-mercaptoethanol, followed by several electrodialysis operations. These treatments have the effect of solubilizing and removing the biological substances (lipids and proteins, especially keratin) which are not bonded in a covalent manner to the structure of the corneous sheath. The purified corneous sheaths are collected, washed, and placed in suspension in physiological serum.

To prepare polyclonal antibodies, antibodies are collected from the serum of immunized animals and purified by conventional methods, for example, by affinity chromatography, so as to retain only the antibodies which recognize the stratum corneum. The antibodies do not recognize the basal and suprabasal cells of either the epidermis used in the preparation of the corneous sheaths employed as immunizing agents, or the normal human epidermis. In addition, the antibodies selected have the other above-mentioned properties.

To prepare monoclonal antibodies, conventional techniques are used to draw off the lymphocytes from the immunized animal. Next, a procedure such as hybridoma cell fusion is performed by fusing the immunized cell lymphocytes cultured in vitro, with, for example, the SP2/0 mouse myeloma cells, by adding polyethylene glycol. The appropriate clones of hybrid cells which secrete monoclonal antibodies having the properties listed above are selected after conventional screening procedures are carried out. Further separation of the selected antibodies produced in the culture medium or in ascites are performed by methods known in the art.

The present invention also relates to hybrid cell lines capable of secreting these antibodies. In particular, the present invention relates to the CIRD BC 21 hybrid cell line deposited at the European Collection of Animal Cell Cultures as No. 89091901, as well as the monoclonal antibodies (BC 21) secreted by this cell line.

The present invention further relates to antibodies attached onto a solid substrate that may be reacted with a radiolabeled, fluorescent label, or enzymatic marker. The monoclonal antibodies specified above may be used as reagents in immunological techniques based on the antigen-antibody reaction. These techniques, such as direct or indirect immunofluorescence, immunoenzymatic techniques and radioimmunological methods are well known in the art.

The present invention further relates to antibodies that may be used, in particular, as biological sensors in techniques which use biological probes to detect molecules carrying the antigenic determinant against which the antibody is directed. The antibodies may serve as reagents used to study the normal or pathological differentiation of the epidermal cells, especially those of the human epidermis. They can be used, in particular, in human medicine for the diagnosis of dermatological diseases and diseases of the internal epithelia. In particular, the antibodies which recognize the keratinized epithelial tissues can be used to determine whether internal epithelia are keratinized. The antibodies of the present invention may be used principally in all medical imaging techniques using antibodies.

The present invention also relates to antibodies that may be used as reagents for the quantification of the epithelial stratum corneum in order to study the variation in thickness of the stratum corneum under the effect of a medication and verify the efficacy of that medication. The antibodies which specifically recognize the stratum corneum in a mammal such as rats, rabbits and miniature pigs have the advantage of making possible the selection of that mammal as a model animal for a study of this kind.

The present invention further relates to antibodies that may also be used in the preparation of medicines, as drug vectors, especially in drugs used in the treatment of disease states linked to keratinization disorders, such as ichthyosis or photo-induced aging, or linked to keratinization disorders with inflammatory components, as in the case of psoriasis or eczema. For example, the antibodies according to the invention which recognize cutaneous tissues affected with psoriasis can be used as drug vectors in the treatment of that affliction, especially antimitotics.

The present invention also relates to antibodies that may be linked by a covalent bond to colloidal vectors such as liposomes (see, for example, Wright and Huang. *Advanced Drug Delivery Review* 3, 343–389, 1989) or polymeric microspheres containing a biologically-active substance or a diagnostic agent, in order to be used as immunoreagents or as therapeutic agents. The biologically active substance is, for example, an antimitotic agent such as methotrexate. These liposomes or microspheres containing antibodies capable of recognizing cutaneous tissues affected with psoriasis may be used, for example, as a medication in human medicine for the treatment of this affection. In this case, the liposomes or microspheres are applied topically.

The following examples illustrate the invention without limiting it.

EXAMPLES

Example 1

Production of Monoclonal Antibodies

1) Preparation of Corneous Sheaths Used As An Antigen

Human epidermis or stratum corneum is incubated for 10 minutes at 90° C. in a solution A (2% SDS, 0.1% DTE, 0.01% sodium azide). During incubation, the corneum sheath suspension is vigorously stirred three times in a vortex. The sample is then centrifuged for 10 minutes at 4000 g and the sediment obtained is put back into suspension in solution A. This entire operation is repeated four times.

The corneous sheath sediment obtained after the final centrifuging process is placed in suspension in solution B (62.5 mM Tris-HCL pH 6.8, 2% SDS, 5% beta-mercaptoethanol, 10% glycerol, 0.025% bromophenol blue). It is then incubated for 10 minutes at 90° C. and transferred to a dialysis bag (Spectrapor 6/132542, marketed by Spectrum Industries). The bag is then immersed in an electrotransfer tank (Transblot, marketed by Biorad) containing a buffer solution C (200 mM glycine, 25 mM Tris, 0.1% SDS). A voltage of 20 V is fed into the tank for 24 hours at 4° C.

The corneous sheaths are then removed and washed by centrifuging in solution C. The residue obtained is once again placed in suspension in buffer solution B. Electrodialysis is repeated three times. After the final electrodialysis, the residue is put back in suspension in distilled water. The suspension is centrifuged for 5 minutes at 4000 g. This operation is repeated three times, then the residue is placed in suspension in physiological serum in a concentration of 1 mg/ml of protein, as determined by the quantitative analysis of Lowry et al. (*J. Biol. Chem.*. 1951, 193, 265–275).

SDS: sodium dodecyl sulfate
DTE: dithioerythritol

2) Immunization

Female Balb/c mice 8 to 11 weeks old are immunized intraperitoneally with 1 mg of corneous sheaths prepared as described above. Three identical procedures are repeated three weeks apart. The spleens of the animals are removed three days before the last repetition.

3) Culture of SP 2/0 mice myeloma cells

Use is made of a line of SP 2/0 cells (Shulman and Kohler, *Nature.* 276, 269, 1978) which cannot survive in a medium containing azaserine and hypoxanthine (Buttin et al., *Cur. Top. Microbiol. Immunol.*, 81, 27, 1978). The cells are cultured in an Eagle medium modified by Dulbecco (DME) containing 4.5 g/l of glucose, 1.2 g/l of sodium bicarbonate, 1 mM of sodium pyruvate, and 2 mM glutamine (i.e., a complete DME medium), to which is added 10% heated foetal calf serum (10 minutes at 56° C.). After defrosting, the SP 2/0 cells must be cultured at concentrations of between $2 \times 10^4$ and $8 \times 10^5$/ml until they have reached a doubling time of 12 to 15 hours. Freezing of these cells takes place in a concentration of $5 \times 10^6$/ml in 95% foetal calf serum and 5% DMSO (dimethyl sulfoxide).

4) Preparation of the SP 2/0 cells

SP 2/0 cells undergoing exponential growth in a concentration of $10^5$ to $2 \times 10^5$ cells per ml are centrifuged at 800 revolutions per minutes for five minutes, and are put back into suspension in DME without serum in the proportion of $10^7$ cells/ml.

5) Preparation of the splenocytes

Splenocytes from immunized mice are prepared conventionally and placed in suspension in a complete DME medium (Dulbecco's modified essential medium) without serum. For counting purposes, 50 μl of the suspension are drawn off and mixed with 50 μl of 0.2% trypan blue and 400 μl of PBS buffer (phosphate buffered saline). After 30 seconds, an aliquot is arranged in a Buerker cell. The suspension is centrifuged at 800 rpm for 5 minutes and adjusted to $10^7$ viable cells/ml.

6) Fusion (day 0)

The technique used is derived from the "mass fusion" technique of Joy et al. (*J. Immunol.* 129, 1153, 1982). The myeloma cells and splenocytes are mixed in a 50-ml polypropylene tube in a ratio of 1 myeloma cells to 4 splenocytes, and are centrifuged at 800 rpm for 5 minutes. The supernatant fluid is pipetted and 1 ml of complete DME without serum is added to the sediment, which is then put back into suspension (Galfre et al., *Nature.* 266, 550, 1977). For $10^7$ splenocytes, 100 μl of polyethylene glycol 4000 (PEG 4000) diluted to 50% in DME containing 5% DMSO are added to the sediment. The DMSO must be added immediately. The added PEG solution is dripped for 1 minute while slowly shaking the tube continuously. After 1 minute resting time at the ambient temperature, 1 ml of complete DME containing 10% foetal calf serum (FCS) is added during 1 minute. The tube is allowed to rest for 1 minute. Next, 15 ml of complete medium containing the foetal calf serum are dripped (approximately 1 ml per minute) while slowly shaking. The suspension obtained is drawn off using a 25-ml pipette and distributed in a culture dish 150 mm in diameter, which is incubated in an oven at 37° C. for 6 hours. The cells are centrifuged at 800 rpm for 5 minutes and put back in selective medium in the proportion of 1 ml of selective medium to $2.5 \times 10^6$ of the original splenocytes. The selective medium has the following composition: complete DME containing $10^{-5}$M azaserine, $10^{-5}$M hypoxanthine, and 2 μl/ml insulin. The suspension is then distributed in culture plates having 24 wells in the proportion of 0.5 ml/well. Under these conditions, hybridoma clones appear between day 5 and day 7 0.2 ml/well of selective medium is added on day 6.

7) Locating hybridomas which produce the sought-for antibodies

When the hybridomas cover one-third of the surface of the wells, the culture supernatant is tested by indirect immunofluorescence on sections of human epidermis using the technique described below.

8) Transfer of the selected wells

When the wells are two-thirds confluent, their content is transferred to 12-well plates. At preconfluence, the hybridomas are cloned using the technique described below. At the same time, they are developed until a confluent T25 bottle (25 cm²) is obtained. These cells are then frozen in the freezing medium described above.

For cloning, the dilution limit technique is used. In a plate having 96 wells, 1 cell/well is seeded. Another plate is also seeded with a theoretical concentration of 0.3 cell/well. The supernatants in the wells are tested by indirect immunofluorescence and the clones which react with all or a part of the epidermis are then cultured and developed in selective medium from which azaserine is absent. After they have been cultured for one week, the clones are cultured in complete DME. Cloning is repeated once under the same conditions.

Using the techniques described in Example 2, the clones secreting antibodies which recognize normal human epidermis are selected out.

From the clones selected (category A), those which recognize specifically the stratum corneum of normal human epidermis (sub-category B) are chosen.

It has been observed that, out of the clones in category A, approximately 5% at least (generally about 5 to 10%) belong to sub-category B.

One clone (CIRD BC 21) obtained under these conditions has been deposited with the European Collection of Animal Cell Cultures, under the number indicated above.

9) Growth of hybridomas in ascites

The growth of the hybridomas obtained in ascitic fluid is carried out by intraperitoneal injection of $10^7$ cells derived from a single clone into 8 week-old BALB/c mice which have been previously sensitized by intraperitoneal injection of 0.5 ml of pristane (2,6,10,14-tetramethyl pentadecyl hydride).

10) Identification of the class of gammaglobulins secreted

The class of gammaglobulins secreted in the myeloma supernatant has been established by double diffusion in agar using reagents specific for the heavy gammaglobulin chains (Serotec Ltd., Bicester, Great Britain). The gammaglobulin secreted by the CIRD BC 21 clone is Ig M.

Example 2

Tissular Specificity of the Antibodies Secreted by the CIRD BC 21 Line

1) Immunofluorescence

The tissular specificity of the antibodies present in the myeloma supernatants and in the ascitic fluids has been studied using the indirect immunofluorescence technique on sections of approximately 5 μm of various frozen tissues and included in an inclusion medium (Tissue-Tek). The dried slides which hold the tissues are rinsed for 10 minutes in a bath of PBS buffer phosphate, then incubated for 30 minutes in a damp atmosphere in the presence of the monoclonal antibodies obtained. Rinsing takes place for 10 minutes. A second thirty-minute incubation is performed in the presence of anti-lgM mice antibodies bonded with FITC (fluorescein isothiocyanate marketed by Cappel). After rinsing under the same conditions as those previously specified, the sections are mounted between slides and cover-slips in the mounting medium (90% glycerol and 10% PBS containing 1% para-phenylene diamine, pH 8). Epithelial tissues from various sources have been used to study the species specificity of the antibodies. Different human epithelial tissues have been used to study their tissular specificity. Human pathological tissues have also been used to evaluate the diagnostic value of the antibodies. Furthermore, there activity of the antibodies has been studied using keratinocytes cultured in conventional cultures (Rheinwald and Green *Cell.* 6 331,1975), in emerged cultures on dead dermis (Regnier et al *Front. Matrix. Biol.* 9, 4, 1981), or on collagen lattices (Lenoir et al., *Dev. Biol.* 130, 610, 1988).

2) Electron Immunomicroscopy

Sections of approximately 10 μm of frozen epidermis in an inclusion medium (Tissue-Tek) are incubated in the presence of monoclonal antibodies, as before. After rinsing, the sections are incubated with the ABC Vectastain kit (Vector Lab.). Fixation of the tissue is achieved using the Graham and Karnovski technique (*J. Biochem. Cytochem.* 14, 291, 1966). The superfine sections, which are dehydrated in aqueous ethanol solutions having various concentrations containing from 70% to 100% alcohol (volume/volume) and then placed in the EPON 812 inclusion medium, are observed under a JEOL 1200 EX electron transmission microscope.

3) Results

The immunofluorescence results thus obtained are summarized in the following tables:

TABLE I

TISSULAR SPECIFICITY IN MAN OF THE ANTIBODY SECRETED BY THE CIRD BC 21

Tissues tested (by indirect immunofluorescence on sections of frozen tissues).

| Skin | Esophagus | Cornea | Vagina | Tongue | Amnion | Duodenum |
|---|---|---|---|---|---|---|
| +++* | — | — | — | −/+() | — | −/+(*) |

*Various sites: Breast, stomach, forehead, prepuce. In all cases, the antibody attaches only on the stratum corneum.
**The keratinized zones are positive, while the unkeratinized zones are negative
***The epithelial cells are negative, while the mucous cells are positive.
+++: high degree of labeling
—: labeling absent

TABLE II

SPECIFICITY OF ANTIBODY SPECIES SECRETED BY CIRD Bc21 LINE

Species tested (by indirect immunofluorescence on sections of frozen tissues

| Mouse[a] | Rat[a] | Rabbit[a,b] | Miniature pig[a] (Gottingen race) |
|---|---|---|---|
| — | +++ | +++ | +++ |

[a]Epidermis: antibodies attach only to the stratum corneum.
[b]Rabbit lip: The outer orthokeratotic zone is positive, while the internal parakeratotic zone is negative.
+++: high degree of labeling
—: labeling absent

TABLE III

CUTANEOUS PATHOLOGY: ABSENCE OR PRESENCE OF REACTIVITY OF THE ANTIBODIES SECRETED BY THE CIRD BC 21 LINE

| Psoriasis (5)[a] | Common Ichthyosis (1) | Spinocellular Carcinomas (4) | Basocellular Carcinomas (4) |
|---|---|---|---|
| +++ | +++ | — | — |

[a]the number in parentheses indicates the number of subjects studied.
+++: high degree of labeling
—: labeling absent

TABLE IV

REACTIVITY OF THE BC 21 ANTIBODIES WITH CULTURED KERATINOCYTES

| Conventional Culture | Culture on Dermis | Lattice Culture |
|---|---|---|
| — | +++ | +++ |

+++: high degree of labeling
—: labeling absent

To summarize, in the case of skin that is normal, psoriasic, or stricken with common ichthyosis, the antibodies secreted by the CIRD BC 21 line react exclusively with the stratum corneum. However, they do not react with the completely differentiated internal zones, or "corneous globes" of the spinocellular carcinomas. The antibodies do not react with stratified unkeratinized epithelia or with single epithelia. However, specific marking of the mucous cells of the duodenum has been observed. The antibodies also react with the stratum corneum of other animal species.

The antibodies do not react with conventionally-cultured keratinocytes, but they strongly label the stratum corneum formed when the keratinocytes are cultured on dead skin or on collagen lattices that are exposed to air. Finally, immunolabelinging electron microscopy on human epidermis has revealed the presence of a specific discontinuous label located in the intercorneocytic space of the stratum corneum.

What is claimed is:

1. A hybridoma cell line having the accession number at the European Collectors of Animal Cell Cultures of No. 89091901.

2. A monoclonal antibody produced by the hybridoma of claim 1 wherein said monoclonal antibody is CIRD BC 21.

* * * * *